United States Patent [19]
Smokvina et al.

[11] Patent Number: 5,688,689
[45] Date of Patent: Nov. 18, 1997

[54] CLONING AND EXPRESSION VECTORS IN AN ACTINOMYCETES STRAIN, PROCESS FOR TRANSFORMATION OF THIS STRAIN, ACTINOMYCETES STRAIN OBTAINED AND PREPARATION OF PROTEINS

[75] Inventors: Tamara Smokvina; Frederic Boccard; Michel Guerineau, all of Paris, France

[73] Assignee: Centre National de la Recherche Scientifique (CNRS), Paris, France

[21] Appl. No.: 477,502

[22] Filed: Jun. 7, 1995

Related U.S. Application Data

[63] Continuation of Ser. No. 995,544, Dec. 22, 1992, abandoned, which is a continuation of Ser. No. 353,749, May 18, 1989, abandoned.

[30] Foreign Application Priority Data

May 18, 1988 [FR] France ................................ 88 06638

[51] Int. Cl.$^6$ ............................ C07H 21/04; C12N 15/64
[52] U.S. Cl. ........................................ 435/320.1; 536/23.1
[58] Field of Search ................................ 435/69.1, 71.2, 435/235.1, 172.3, 252.3, 320.1; 536/23.1

[56] References Cited

U.S. PATENT DOCUMENTS 4,743,546  5/1988  Backman ................................ 435/108

FOREIGN PATENT DOCUMENTS 0191643  8/1986  European Pat. Off. .
0235112  9/1987  European Pat. Off. .
0243856  10/1987  European Pat. Off. .

OTHER PUBLICATIONS

Gray et al, "Synthesis of bovine growth hormone by *Streptomyces lividans*", Gene 32:21–30 (1984).
"Isolation and characterization of the *Streptomyces cattleya* temperate phage TG1", Gene 39:11–16 (1985).
Pernodet et al (FA 411853) "Plasmids in Different Strains of *Streptomyces ambofaciens*: free and integrated form of plasmid pSAM2", Mol. Gen. Genet. 198:35–41 (1984).
Chemical Abstracts vol. 105, Aug. 4, 1986, 1–pharmacology, No. 5 3440u.
Chemical Abstracts vol. 99, Dec. 12, 1983, No. 24, p. 191 207354h (Chemical Abstracts of Japan).
Kirby et al (1975), Nature, vol. 25A, pp. 265–267.
Thompson et al (1982), Gene, vol. 20, pp. 51–62.
Omer et al (1986), Journel of Bacteriology, vol. 166, pp. 599–1006.
Cloning Vectors (1985), A Laboratory Manual (Elsevier, NY).
Simonet et al (1987), Gene, vol. 59, pp. 137–144.
Pierson et al (1984), Mol. Gen. Genet., vol. 156, pp. 44–51.
Omer et al, "site–Specific Insertion of Biologically Functional Adventitious Genes into the *Streptomyces lividans* Chromosome", Journal of Bacteriology, May 1984, pp. 2174–2184.
George et al (1988) "Current methods in sequence comparison anad analysis" in Macromolecular Sequencing and Synthesis, Seelcted Methods & Applications, ed. Schlesinger, Alan R. Liss, Inc., NY pp. 127–149.

*Primary Examiner*—George C. Elliott
*Assistant Examiner*—Andrew Wang
*Attorney, Agent, or Firm*—Cushman Darby & Cushman Intellectual Property Group of Pillsbury Madison & Sutro LLP

[57] ABSTRACT

The present invention relates to a vector for cloning and expression of a DNA sequence coding for a particular protein in an Actynomycetes strain. The process comprises:
- an attachment sequence att,
- a DNA sequence coding for an int sequnce functional in said strain, and
- a DNA sequence coding for said specific protein and for the elements ensuring the expression of said sequence in said strain.

5 Claims, 13 Drawing Sheets

Fig. 3A

```
                                                                            160
                              nValValGluLeuCysSerValProGlnGlyArgProSerLysAlaLeuThrPheAlaGlnAlaGl
                              CGTGGTGGAGCTGTGCTCTGTGCCGGGCCTGGCCGTTCCAAGGCGCTCACCTTTGCCCAGGCCGA   711
                                          180
                              uAlaValLeuAsnAlaAlaGluGlyThrSerMetHisAlaTyrIleValValAlaAlaLeuLeuThrGlyAlaArgTh
                              GGCCGTGGTGCTGAATGCTGCCGAGGGCACGTCGATGCACGCCTACATCGTCGTCGCCGCTCTGCTGACCGGTGCCGCGCAC   636
                                          205
                              rGluGluLeuArgAlaLeuThrTrpAspHisValPheLeuLysGlyGlySerProAspValGluProProGlnProPr
                              CGAGGAGCTGCGGGCGCTGACCTGGGACCACGTCTTCCTCAAGGGAAGTCCGGACGTTGAGCCGCCGCAGCCTCC   561
                                          230
                              oHisIleAlaValTrpArgSerValArgArgGlyGlyAspThrLysSerArgArgThrLeuAlaLe
                              GCACATCGCCGTCTGGCGCTCGGTCCGGCGCGGTGGGGACACGAAAACCCGGAAGTCTCGGCGAACGCTCGCCCT   486
                                          255
                              uProAlaArgCysValGluValLeuTrpGlnGlyTrpGluAspGlnGlyTrpArgLeuAlaAlaGlyAspLy
                              GCCGGCGCGTTGCGTGGAGGTCCTGTGGCAGGGCTGGGAAGACCAGGGCTGGAACGGCTCGCCGGTGACAA   411
                                          280
                              sTrpGluGluHisGlyLeuValPheSerSerAlaValGlyLysProLeuAspAlaThrAsnValArgArgAlaPh
                              GTGGGAGGAACACGGCCTGGTCTTCTCGTCCGCCGTTGGCAAGCCGCTCGACGCGACTAACGTCCGGCGCGCCTT   336
                                          305
```

Fig. 3B

```
310                        320
eArgGlnAlaLeuLysAspAlaAsnGlyIleAsnAlaAspGluTrpThrProArgGluLeuArgHisSerPheVa
CGCCAGGGCGCTCAAGGATGCCAACGGGATCAACGCCGACGAGTGGACACCGAGGGAGCTGAGGCACAGCTTCGT   261

335                        345
lSerLeuLeuSerAspArgLeuGluGluIleSerArgLeuValGlyValProLeuGluGluIleSerGlyThrAlaValTh
GTCCCTGCTCTCCGACCGCGGCGTCCCGCTGGAGGAGATCTCCGGACTCCGGTACGGCCGTGAC               186

360                        370                        380
rGluGluValTyrAraLysGlnIleIleArgProValIleGlnThrGlyAlaAlaValValMetAspGlyIlePheLysAr
TGAGGAGGTCTACCGGAAGCAGATCCGGCCCGTCATCCAGACCGGCGCTGTGGTCATGGACGGCATCTTCAAGCG      111

385
gGlyProAlaArg***
GGGTCCGGCGCGATAGTCACGCGCAGATAGACACGCACAGAAAACAGGTGAGGCAGACCGTAACGGTTACGGTCTGCC    36

TCACCTGGTGT | TTCTCTGTCGGGTGGGGGGATTTGAACCCAGACCTCTTCGTCCCGAA |                   -24
```

Fig. 3C

```
CGCCACCATCGCCCGGAACCTCCAGCTCAACCGGAGACAGCTCGTGAAGCCGTACGCGACCAACTCGACCAGGA    1461
                                                               20
               MetThrThrValThrProGluLeuLeuThrValProGluValMetAlaArgLeuLysValGly
               1                          10
AGGAGTCGCAGCATGACCACCGTCACTCCAGAGCTGCTGACCGTGCCGGAAGTCATGGCGGCGCTGAAGGTTGGA    1386
                                 35                                 45
ArgSerLysSerThrThrSerSerAlaProAlaAlaLeuProProSerArgSerThrGluArgValGluTyrPro
    25
CGCAGCAAGTCTACGACCTCATCCGCCCCGCCCTTGCCTCCATCAAGATCGACGGAGCGGTCGAGTACCCA      1311
ProThrProTyrAlaThrSerPheArgThrSerTrpGluArgProSerAspGlyGlnAlaThr***
    50                                 60
                                                                       MetAlaLysArgArgSerArgGlyAs
                                                                       1
CCGACGCCCGTACGGCGACTTCATTCAGGACCAGTTGGGAGAGGCCATTCTGATGGCCAAGCGACGTAGCCGGGGGTGA   1236
pGlyGlyLeuHisTrpAspGluLysArgGlnArgTrpIleAlaThrAlaAsnLeuGlyPheAspProSerGlyLy
  10                              20                            30
CGGCGGCCCTCCACTGGGACTGGAGACGAGAGACAGCGCTGATCGCCACGGCCGAACCTCGGCTTCGATCCGAGCGGTAA   1161
```

Fig. 3D

```
 35                          45                           55
sArgIleValLysArgGlySerGlyLysThrGluAlaAlaLysAsnLysLeuLysGluValLeuArgAspHi
GCGGATCGTCAAGCGGGGGAGTGGCAAGACCGAGGCCAAGAACAAGCTCAAAGAGGTTCTGCGTGACCA    1086

60                          70                           80
sGluAspGlyLeuAlaIleAlaProThrGlyTyrThrValAlaAspAlaValAlaAsnAspTrpLeuAlaTyrGlyLeuLe
CGAAGACGGTCTCGCGATCGCACCCACGGGGTACACCGTCGCCGACGCGGTGAACGACTGGCTTGCCTACGGTCT        1011

85                          95                          105
uAlaGlyArgAspGlnArgThrValGluAsnCysThrHisLeuSerGlnLysHisValIleProGlyLeuGlyAl
CGCTGGCCGGTCGCGACCAGCGCACCGTCGAGAACTGCACCCACCTAAGCCAGAAGCACGTCATACCGGGTTTGGGTGC    936

110                         120                         130
aArgLysLeuArgAspLeuSerAlaGluAspValAspArgTrpLeuAlaAlaAlaLysAlaAlaGlnThrLeuSerThrAr
CCGGAAGCTGCGTGACCTCAGCGAAGACGTCGACAGAGACGTCGGCCGCCAAGGCTGCCGCCAAGGCTCAGACTCTGAGCACGCG  861

135                         145                         155
gSerLeuGlnAlaValHisSerCysLeuAsnArgAlaValLysArgAspAlaMetAlaArgAlaValLysArgAs
CAGCCTTCAGGCGGTCCACTCCTGCCTGAACCGGGCCGTCAAGCGGGACGCCATGGCCCGTGCCGTGAAGCGCAA       786
```

Fig. 7

5'-GATCCGAGCTCGGTACCCTCTAGACTCGAGAAGCTTGAATTCA-3'
3'-GCTCGAGCCATGGAGATCTGAGCTCTTCGAACTTAAGTCTAG-5'

Fig. 9

5' GATCAAGCTTCTGCAGGCATGCTCTAGACTCGAGGAATTC 3'
3' TTCGAAGACGTCCGTACGAGATCTGAGCTCCTTAAGCTAG 5'

CLONING AND EXPRESSION VECTORS IN AN ACTINOMYCETES STRAIN, PROCESS FOR TRANSFORMATION OF THIS STRAIN, ACTINOMYCETES STRAIN OBTAINED AND PREPARATION OF PROTEINS

This is a continuation of application Ser. No. 07/995,544, filed Dec. 22, 1992, now abandoned, which is a continuation of application Ser. No. 07/353,749, filed May 18, 1989, now abandoned.

BACKGROUND OF THE INVENTION

The present invention relates to cloning and expression vectors of proteins in Actinomycetes as well as strains transformed by these vectors.

Bacteria belonging to the order of actinomycetes, and in particular those of the genus Streptomyces occupy a particularly important place in industrial microbiology. In fact, since the discovery by Waksman of a Streptomyces strain producing streptomycin, many other strains of antibiotic producing Streptomyces have been isolated and exploited industrially during the last forty years. The richness and diversity of the secondary metabolites produced by Streptomyces are illustrated by the fact that the latter synthesize 55% of the natural antibiotics recorded up to 1978. About 70% of the antibiotics produced industrially are manufactured through Streptomyces. Secondary metabolites of microbial origin have especially been used for their antibacterial, antifungal or antitumoral activity. Substances possessing these types of activity have been discovered in very great number during the period 1950-1970. At present, the rhythm of discoveries for these types of application has slowed down but the total richness of microbial secondary metabolites is far from having been exploited. In fact, many fields of use are at present being explored; they relate to antiparasitic agents, insecticides, herbicides or pharmacological applications of these products. In these fields also the products of Streptomyces are many: there may be mentioned monensine which dominates the market of products against coccidiosis, avermectins very active against parasitic nematodes of cattle and possessing also an insecticidal activity, nikkomycins blocking the synthesis of chitin and therefore possessing insecticidal activity. The Streptomyces also produce substances interesting for their pharmacological activity such as anti-inflammatory agents and vasodilatators.

Another reason for interest in the Streptomyces is their use as host for the expression of heterological genes. In fact, many industrial groups possess the knowhow and the equipment necessary to cultivate Streptomyces and exploit these cultures. A culture in stationary phase can remain metabolically active for several weeks and continue to synthesize proteins and secondary metabolites. Considering that Streptomyces produce a large number of extracellular enzymes, of which several are used industrially such as proteases or glucose-isomerase, their excretion system could be used for the production of heterologous proteins. Streptomyceses lividans has already been employed with success as a host for the expression of bovine growth hormone by the Biogen Company (Gray et coll., 1985).

The use of the strain Streptomyses ambofaciens is particularly taken up for the production of spiramycin, an antibiotic of the family of macrolides produced by Rhone-Poulenc. In addition, it is a strain which seems not to exhibit a restriction phenomenon with respect to foreign DNA (Cox et coll., 1984), which facilitates molecular cloning experiments. The principal teams working on the macrolide producing Streptomyces and hence using S. ambofaciens are those of Prof. Omura of Japan, that of R. H. Baltz of the Eli Lilly Company in the United States and that of Dr. A Sabatier of the Rhone Poulenc Sante Company.

The team of S. Omura is principally interested in the paths of biosynthesis of the macrolides, in the discovery of new macrolides and in the production of hybrid macrolides (Omura, 1984). The Baltz team works particularly with S. fradiae and S. erythraeus producing respectively tylosine and erythromycin (Baltz et coll., 1983), but uses S. ambofaciens as host in many molecular cloning experiments (Kuhstoss and Rao, 1983; Matsuhima and Baltz, 1985). It is following the study of several strains of Streptomyces ambofaciens belonging to two isolates of different geographical origin that the presence of a particular plasmid has been detected: the plasmid pSAM2 (Mol. Gen. Genet. (1984) 198:35–41. "Plasmids in different strains of Streptomyces ambofaciens: free and integrated form of plasmid pSAM2"; et Gene, 59 (1987) 137–144 "Excision and integration of a self-transmissible replicon of Streptomyces ambofaciens").

The plasmid pSAM2 has a size of 11 kb, can exist in the free and/or integrated state and has been shown to be capable of transfer from one strain to another. The phenomenon of integration of the plasmid pSAM2 in the chromosome of receptor strains has also been demonstratable but this phenomenon has not been elucidated at the present time.

GENERAL DESCRIPTION OF THE INVENTION

Accordingly, the present invention relates to a cloning and expression vector of a DNA sequence coding for a particular protein in an Actinomycetes strain, characterized in that it comprises:

an attachment sequence att, a DNA sequence coding for a functional int sequence in said strain, and a DNA sequence coding for said specific protein and for the elements ensuring the expression of said sequence in said strain.

This vector is more particularly intended to be an expression vector coding for a protein having interest in itself or indeed facilitating the production of secondary metabolites such as those described previously, in particular antibacterial agents, antifungal agents, antitumoral agents, and proteins such as enzymes, which are already obtained from an Actinomycetes strain or which can be produced by other organmntsms.

Among the art sequences, must be mentioned more particularly the sequences selected from among:

the sequence

TTCTCTGTCGGGGTGGCGGGATTTGAACCCA CGACCTCTTCGTCCCGAA, the sequence having at least 50% homology with this sequence.

In fact, the invention has demonstrated that the chromosomic integration mechanism of the plasmid pSAM2 involves an attachment sequence characterized by this type of nucleotide sequence.

The restriction map of pSAM2 was determined and it is shown in FIG. 1. The attachment sequence is framed in FIGS. 3A–3D; it starts at position +24 and finishes at position −24. The nucleotide at position 0 corresponds to the center of the attachment site.

The vectors according to the invention comprise, in addition, a sequence coding for a functional int sequence in said strain. It is a sequence coding for an integrase, which sequence generally precedes or is situated in the vicinity of the attachment sequence (see FIG. 2). The int sequence plays an important role in the integration phenomenon.

The nucleotide sequence corresponding to this gene int has been determined and it is shown in FIGS. 3A–3D: it corresponds to a DNA sequence comprised between the positions +1261 and +97. This int sequence is mostly preceded, or partially straddled by the xis gene which is the gene coding for excision. The sequence of this gene is also shown in FIG. 3.

The vectors according to the present invention have for the most part the property of being integrated in chromosomes with very great stability.

In order to obtain a large number of vector copies per genome in plasmid form, selfreplicable, with also a copy integrated or unintegrated in the chromosome, it is interesting to resort to vectors in which a fragment of 600 bp has been deleted from each side of the EcoRI site no° 33 of pSAM2, that is to say deleted essentially from a fragment which extends between two repeated sequences situated on each side of the EcoRI site no° 33 (see FIG. 1). In addition, these vectors can contain fragments bearing int and xis genes.

The vectors so obtained show the property of multiplying in very large number.

Like all cloning or expression vectors, elements coming from bacteria will preferably be inserted, in particular from E. coli, in order to enable the construction of vectors in these bacteria, but on exploitation in Actinomycetes strains, these fragments corresponding to E. coli bacteria could be eliminated. The elements usable in bacterial constructions are known; they are mostly of replication origin enabling the plasmids to be multiplied, possibly with a functional resistance in said plasmids and if necessary, other elements facilitating mounting in E. coli.

The DNA sequence coding for said specific protein and for elements ensuring the expression of said sequence in said strain may be inserted at different places in the vector.

When it is desired to prepare an Actinomycetes strain producing a particular protein of which the DNA sequence is integrated in the chromosome, preferably a vector will be used such as described previously and in which the DNA sequence concerned is integrated outside the sequences att and int; in this case integration in the chromosome will be facilitated.

When, on the contrary, it is desirable that this plasmid be not totally integratable into the chromosome, the DNA sequence concerned can be inserted in the int gene.

In certain cases where it will be desired that the vector plasmid should not be transferable from one strain to another, the DNA sequence coding for the particular protein could be inserted at the level of the sequences coding for the functional transfer functions of the transformed strain.

Among the sequences coding for a particular protein, may be mentioned the sequences coding for resistance to certain types of antibiotic, particularly sequences coding for resistance to Thiostrepton.

The resistance to Thiostrepton could, in certain cases, be used as a labelling gene. In this case, if it is desired to express another protein, it will be necessary to provide another cloning site; this could be done, for example, by means of a polyvalent vector, by inserting in one of the vectors described previously a "polylinker" sequence.

In the latter case, the labelling gene is, preferably, placed after the attachment site in the vectors of the invention.

As for the "polylinker" sequence, it is hence, preferably, located downstream of the labelling gene, with respect to the attachment site, the vector obtained being then an integrating vector. A very particularly preferred example is the vector pTS55 described in example 1 below.

Among the integrating and replicating vectors obtained within the scope of the present invention, the position of the "polylinker" sequence can be modified so that the vectors obtained are incapable of being transferred from one strain to another.

Such vectors may be useful particularly in the case of foreign genes coding for proteins particularly advantageous for human or animal health.

By way of example, may be mentioned the vector pTS12, of which the structure will be explained in the following examples.

The "polylinker" sequence may also be located upstream of the labelling gene, namely in the int gene, so that the vector obtained cannot be integrated in the chromosome of the receptor strains. By way of example, may be mentioned, the vector pTS13 whose structure will be detailed in the following examples.

The vectors of the present invention are particularly advantageous by reason of their stability and their specific integration with a wide host spectrum.

Their stability enables recourse to any selection pressure for maintaining the gene in the integral state to be avoided.

In the case of replicating vectors, it may be thought that the vectors also integrating are the most stable; the integrated copy can then provide in a way a matrix enabling the free plasmid forms to be regenerated.

The vectors according to the invention may, in addition, be integrated in all strains possessing the previously defined integration site, namely a site having a sequence comprising in totality or in part the nucleotide sequence of the position +24 to −24 described in FIGS. 3A–3D. This site has been detected by hybridation with a probe going from position +21 to −18 in S. antibioticus (DSM 40868), S. bikiniensis (ATCC 11062), S. parvulus (ATCC 12434), S. glaucescens (ETH 22794), S. actuosus (ATCC 25421), S. coelicolor (A3(2)), S. ambofaciens, S. lividans TK64 (66), and S. griseofuscus (DSM 40191).

For this latter strain, it was noticed that the fourth nucleoitide, namely the nucleotide at position +21, was not thymidine (T) but an adenine (A).

Such a replacement does not affect the possibility of integration with the vectors of the present invention.

In general, at least 50% of the nucleotides must remain unchanged for the possibility of integration not to be affected.

The present invention relates also to the process and preparation of a strain of Actinomycetes producing a particular protein whose DNA sequence is:

either integrated in the chromosome, the DNA sequence concerned being inserted outside of the sequences att and int; preferably, this DNA sequence is inserted in the sequences coding for the transfer function;

or integrated in a plasmid not integrable totally in the chromosome characterized in that the DNA sequence concerned is integrated in the int gene.

The present invention extends to Actinomycetes strains, in particular Streptomyces, transformed by the vectors of the present invention. The present invention relates also to the industrial use of these transformed strains, and this, particularly, for producing a particular protein, by fermentation of a transformed strain according to the present invention in a suitable culture medium and recovery of the particular protein.

A great many proteins may be prepared by means of the vectors of the present invention.

Thus, certain vectors will be more particularly adapted to proteins of which a strong expression is not desired. This is, especially, vector pTS55 which enables the integration of a single gene in the chromosome. There is hence a single copy of the plasmid per transformed cell. Such a vector is suitable for the expression of enzymatic proteins such as amylase or regulation genes acting on the production of proteins or industrially interesting metabolites.

Other vectors will be suitable rather for the expression of foreign proteins of which considerable expression is required. Thus the vectors pTS13 and pTS12, due to the fact of the deletion on each side of the EcoRI no 33 site of the pSAM2 (see the following examples), are maintained at a very high level of copies when they are introduced into Streptomyces and especially *Streptomyces lividans* TK64. The number of copies is greater than 100 per genome.

BRIEF DESCRIPTION OF THE DRAWINGS

The present invention is illustrated by means of the examples and the following figures:

FIGS. 3A–3D represent the sequence of the region comprised between Tth111 no 2 and the integration site att of pSAM2 whose restriction site is shown in FIG. 2; it is the nucleotide sequence of the plasmid pSAM2, the sequence was determined from 70 nucleotides after the site Tth111 no 2 up to the integration site (att), the nucleotide 0 corresponds to the att medium;

FIG. 7 shows the sequence of oligonucleotides introduced into pTS54 in order to construct pTS55;

FIG. 9 shows the sequence of oligonucleotides introduced into pTS11 in order to construct pTS12 and pTS13;

DESCRIPTION OF PREFERRED EMBODIMENTS

EXAMPLE 1

Construction of the integrating vector pTS55

Figure 4:
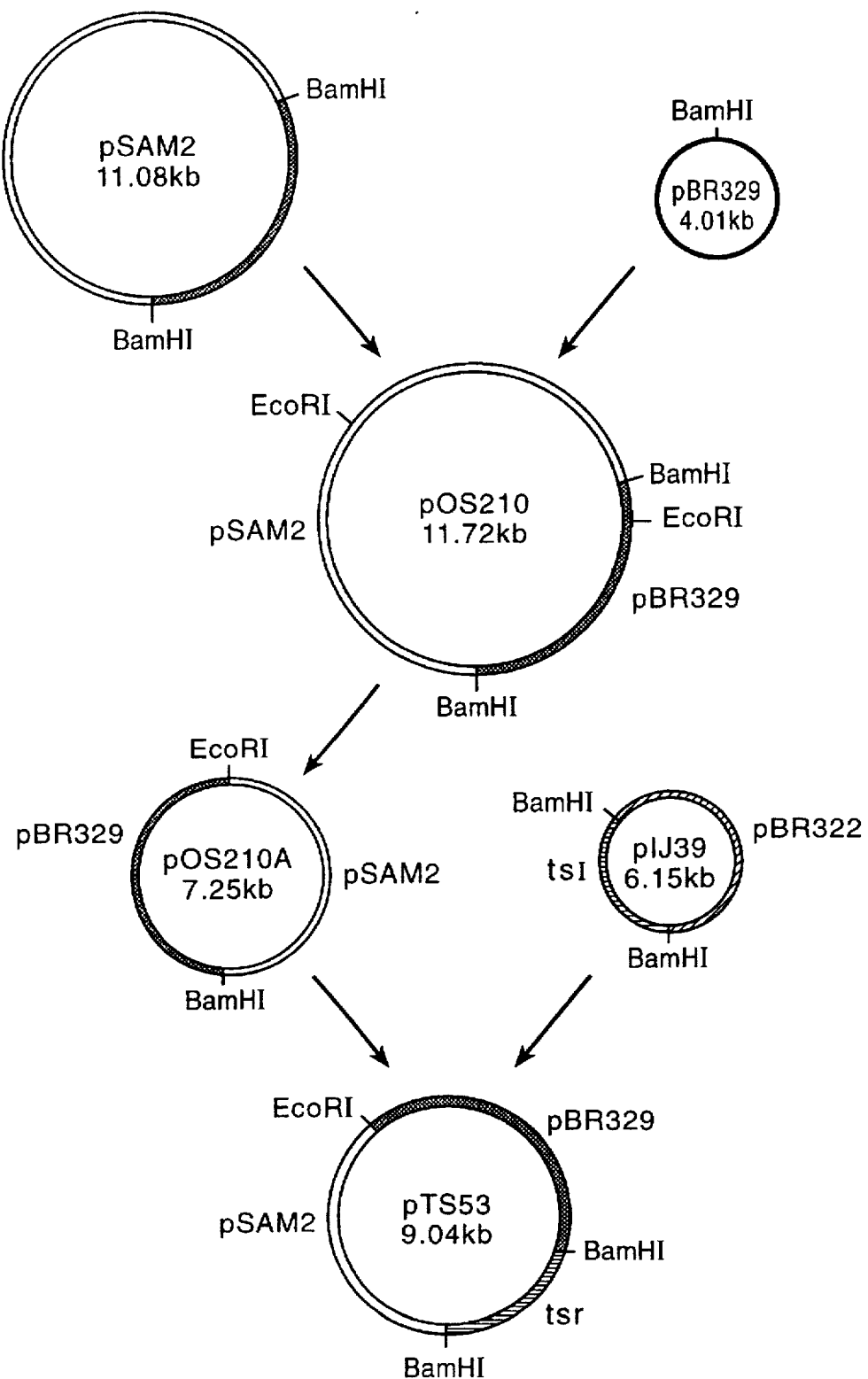
FIG. 4 shows diagramatically the construction of pTS53.

The plasmid pSAM2 (FIG. 1) was extracted and purified from *Streptomyces ambofaciens* (JI3212) by the method of alkaline lysis described by Hopwood in "Genetic Manipulation of Streptomyces" (A Laboratory Manual, 1985).
1st step:

The plasmid pSAM2 was digested with the restriction enzyme BamHI and a fragment of 7.57 kb (kb:kilobase) was isolated and cloned at the BamHI site of the plasmid pBR329, which gave the plasmid pOS210 (FIG. 4).

2nd step:

The plasmid pOS210 was digested with EcoRI and the fragment of 7.25 kb which contains the fragment of pSAM2 from the BamHI no 27 site to the EcoRI no 33 site and the fragment BamHI-EcoRI of 3.55 kb of the plasmid pBR329 was isolated and closed up on itself, which gave the plasmid pOS210A (FIG. 4).
3rd step:

The plasmid PIJ39 corresponds to the plasmid pBR322 which contains the gene conferring resistance to thiostrepton borne by a BamHI fragment of 1.8 kb of *Streptomyces azureus* (Thompson C. J.; Ward J. M.; Hopwood D. A., Nature 286, 525–527, 1980).

The plasmid pIJ39 was digested by BamHI and the fragment of 1.8 kb carrying the resistance to thiostrepton was isolated and mixed with the plasmid pOS210A digested by BamHI (BamHI is a unique site in pOS210A).
4th step:

The plasmid pTS52 contains two BamHI sites and has a size of 9.08 kb. It is digested partially with BamHI and the linearized plasmid of 9.08 kb was isolated. It was treated with the Klenow fragment of polymerase 1 then closed up on itself to eliminate one of the two BamHI sites.

Figure 5:
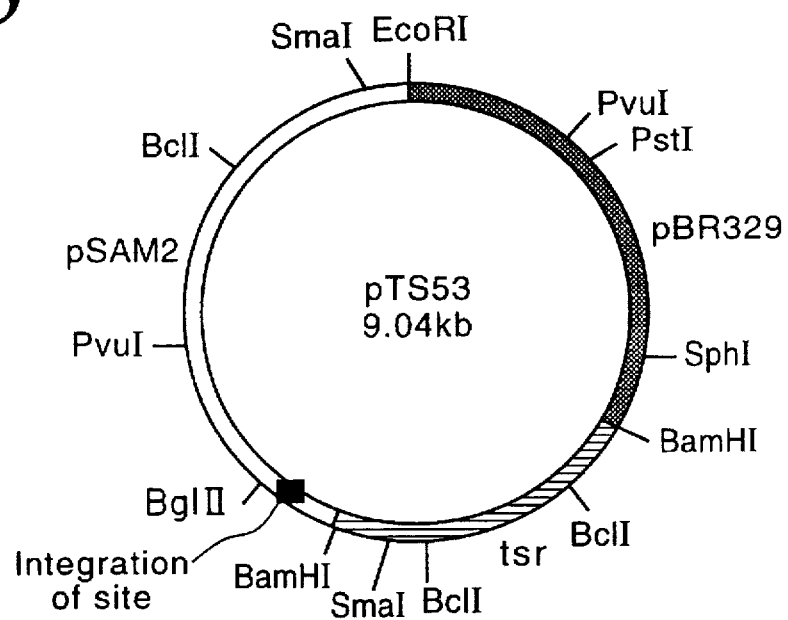
FIG. 5 shows the restriction chart of the vector pTS53.

The plasmid pTS54 carrying a single BamHI site located between the sites SphI and BclI is obtained (FIG. 5).
5th step:

The polylinker double strand oligonucleotide having the sequence described in FIG. 7 was synthesized with the "Applied biosystem" apparatus.

The plasmid pTS55 digested with BamHI was mixed with the polylinker oligonucleotide and ligatured by means of ligase from phage T4.

Figure 6:
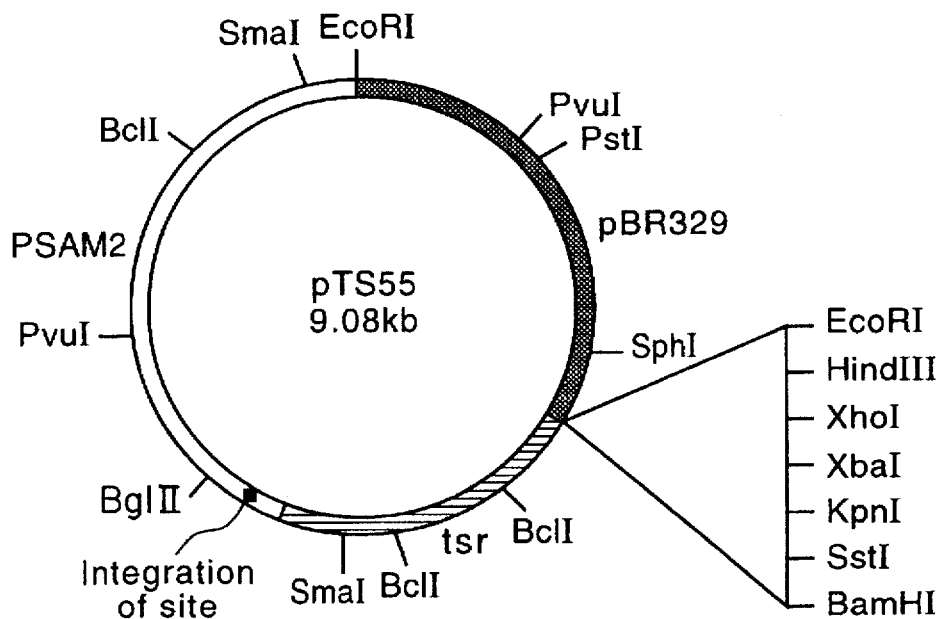
FIG. 6 shows the restriction chart of the integrating vector pTS55.

The resulting plasmid pTS55 is described in FIG. 6. It possesses the following unique restriction sites, available for the clonings: XbaI, XhoI, HindIII, KpnI, SacI, BamHI, and SphI.

The vector pTS55 can be maintained in *E. coli* by selecting for resistance to ampicillin.

By digestion with the restriction enzyme EcoRI the part pBR329 may be withdrawn since it is not indispensible for the integration into the chromosome of Streptomyces. One can hence obtain integrating transformants of Streptomyces which only contain the DNA of Streptomyces.

In the Streptomyces transformants, it confers resistance to the antibiotic Thiostrepton or Nosiheptide.

Figure 2:
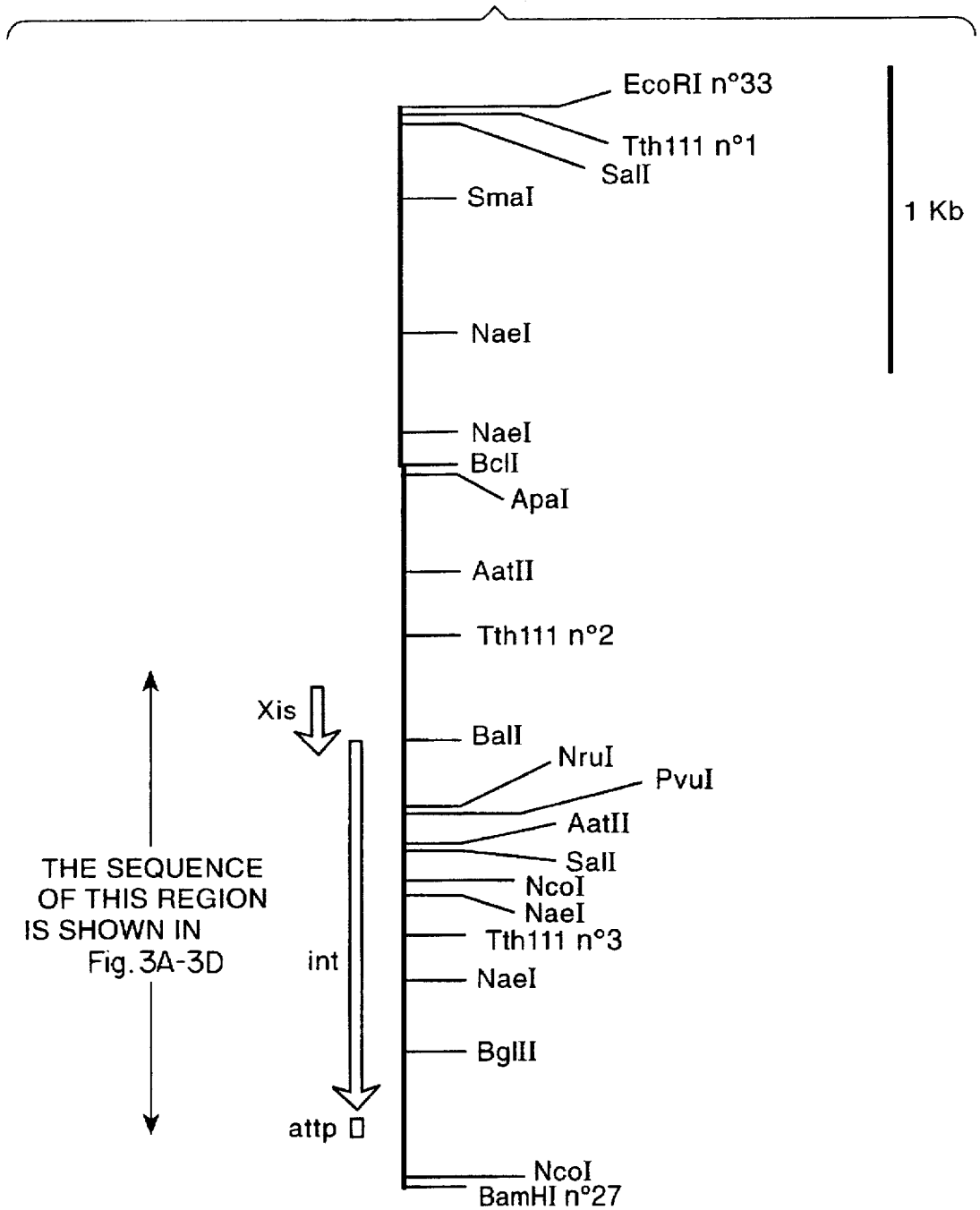
FIG. 2 shows the restriction chart of the fragment Bam/HI-EcoRI of pSAM2 sufficient for integration; this fragment goes from site BamHI-EcoRI to site BamHI no 27 to site EcoRI no 33.

It bears the fragment BamHI-EcoRI of pSAM2 and the nucleotide sequence from the site Tth111 no° 2 to the integration site of the plasmid located between BgIII and BamHI was realized (see FIG. 2) and is described in FIGS. 3A–3D.

The coding phase which starts from the position +1261 and ends at the position +97 corresponds to the integrase required for the integration of the plasmid in the chromosome. The coding phase which starts from the position +1448 and ends at the position +1247 can correspond to the xis gene.

The framed sequence which starts from the position +24 and ends with the position −24 correspond to integration site of the plasma (att). The nucleotide position 0 corresponds to the center of the attachment site. It can be introduced by transformation into Streptomyces according to the technique described in the "Laboratory Manual". It is specifically integrated in the following strains:

*S. ambofaciens*

*S. lividans* TK64

*S. griseofuscus*.

It can be integrated in all the strains possessing an integration site for the plasmid. The site can be defined as having a similar sequence or comprising in totality or in part the nucleotide sequence from the position +24 to -24 described in FIG. 3. This site has been detected by hybridization with a probe going from position +21 to -18 in (FIGS. 3A-3D) in *S. antibioticus, S. bikiniensis, S. parvulus, S. actuosus, S. coelicolor, S. glaucescens*.

This vector permits the integration of a gene in the chromosome at a specific site. Hence there is only one copy per cell, the integration is very stable, and it is therefore not necessary to maintain a selection pressure in order that the gene introduced remain integrated.

EXAMPLE 2

Construction and properties of the free vector pTS39 a) construction

The plasmid pSAM2 originating from *S. ambofaciens* JI3212 is digested partially with EcoRI and the linearized plasmid of 11 kb is isolated and cloned in the EcoRI site of the plasmid PIJ39 (previously described). The resulting plasmid pTS39 contains the plasmid pIJ39 cloned to the EcoRI site no 22 from the plasmid pSAM2 (restriction chart pSAM2, FIG. 1).

b) properties

The plasmid can be introduced by transformation in different strains of Streptomyces where it is maintained in the free state and integrated by conferring resistance to Thiostrepton and Nosiheptide. It is a vector with a wide host spectrum. The number of copies is comprised between 5 and 20 copies per genome.

EXAMPLE 3

Construction and properties of the vector pOS11

1st step:

The pOS7 plasmid has been described in the article of J. M. Simonet et al., p. 137–144, 1987. The two fragments BamHI of 0.88 kb (BamHI No 15 to 21) and of 1.01 kb (BamHI No 21 to 27) of pSAM2 (FIG. 1) were deleted and replaced by the BamHI fragment of 1.79 kb of *S. azureus* conferring the resistance to Thiostrepton and to Nosiheptide.

Figure 8:
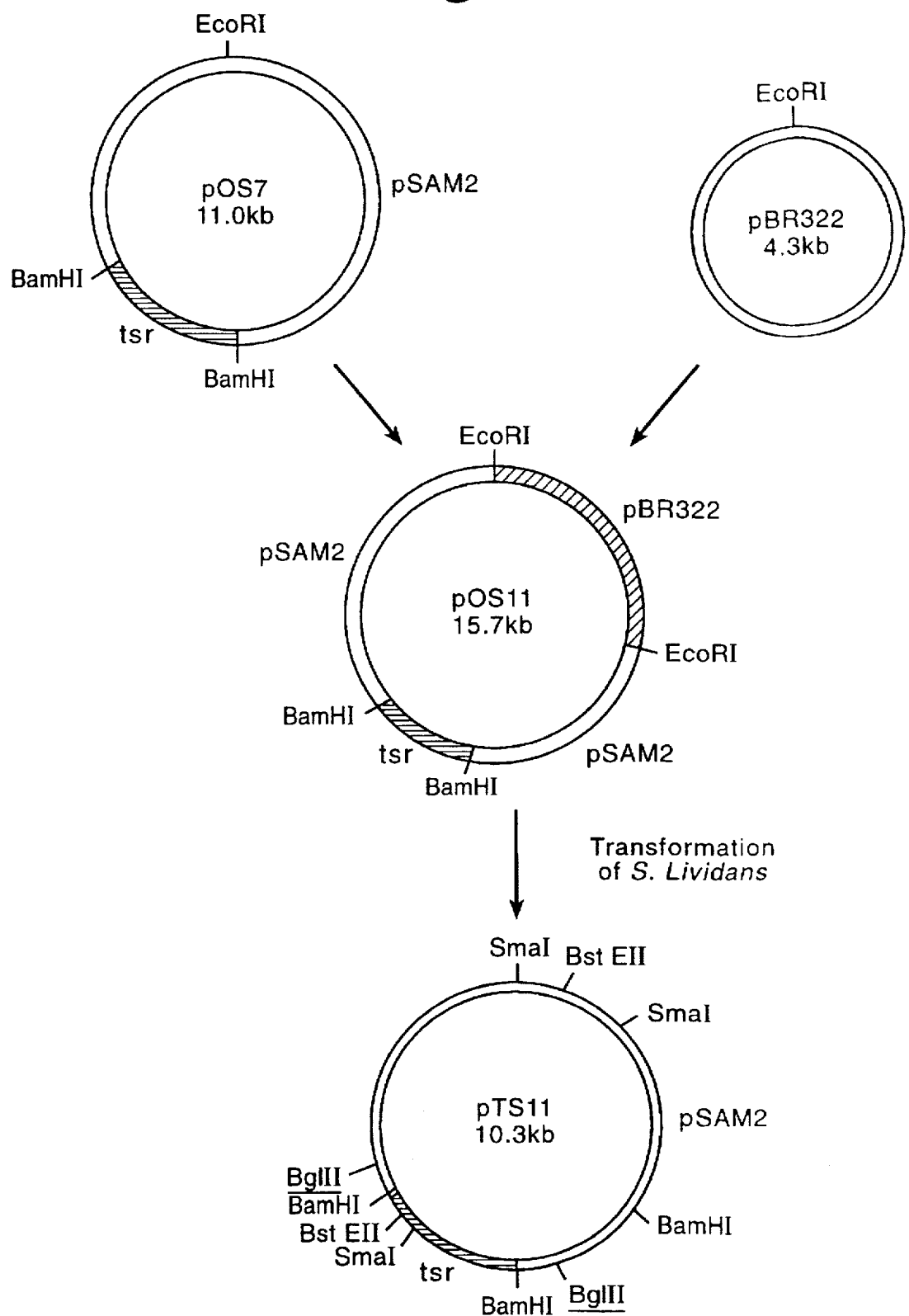
FIG. 8 shows diagramatically the construction of pTS11.

The plasmid pOS7 and the plasmid pBBR322 were digested by EcoRI, mixed and ligatured. The resulting plasmid, pOS11, is obtained. It contains pBR322 cloned to the EcoRI no 33 site of pSAM2 (see FIG. 8).

2nd step:

By transformation according to the usual method, it is introduced into the *S. lividans* where it confers resistance to Thiostrepton and Nosiheptide.

From a transforming clone of *S. lividans* the plasmid pTS11 (FIG. 8), was extracted.

This plasmid no longer contains the plasmid pBR322, and has undergone a deletion of 600 pairs of bases situated on each site no 33 of pSAM2. The PvuII No 1 site and the ApaI no 1 bis site have disappeared (see restriction chart pSAM2, FIG. 1)

3rd step:

The pTS11 plasmid (FIG. 10) is digested partially with BglII in order to linearize the plasmid which has a size of 10.3 kb. The linear molecules having the size of the plasmid are isolated.

Figure 10:
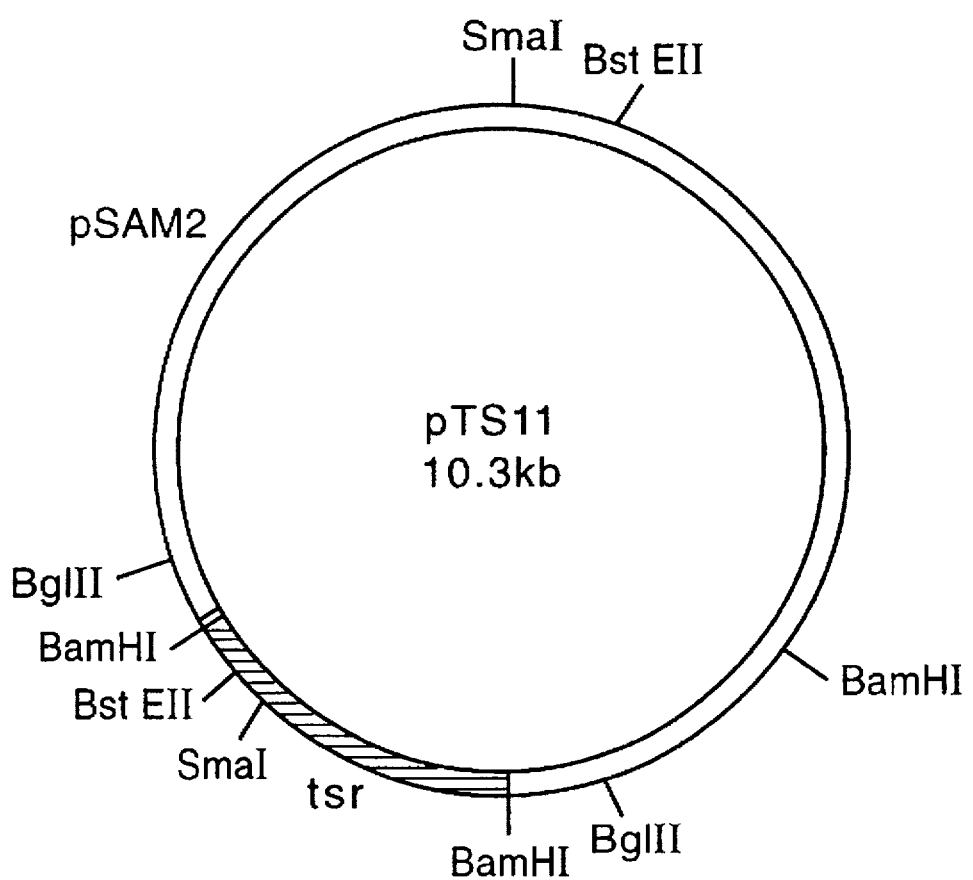
FIG. 10 represents the restriction chart of pTS11.

The polylinker oligonucleotide having the sequence described in FIG. 10 is synthesized.

Figure 11:
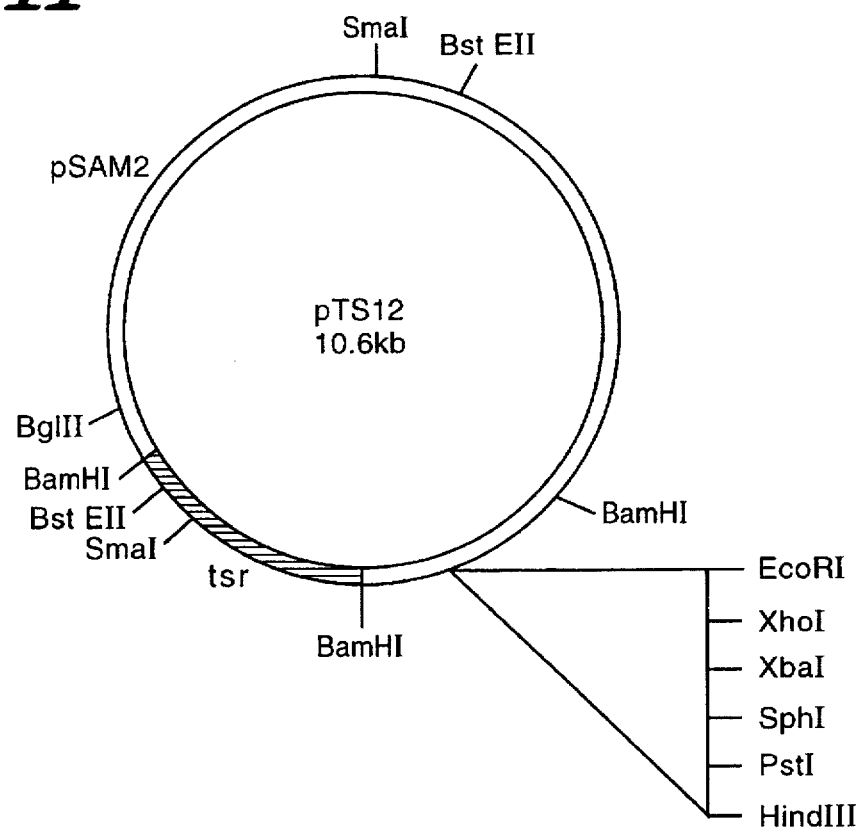
FIG. 11 shows the restriction chart of the multicopy plasmid pTS12.
Figure 12:
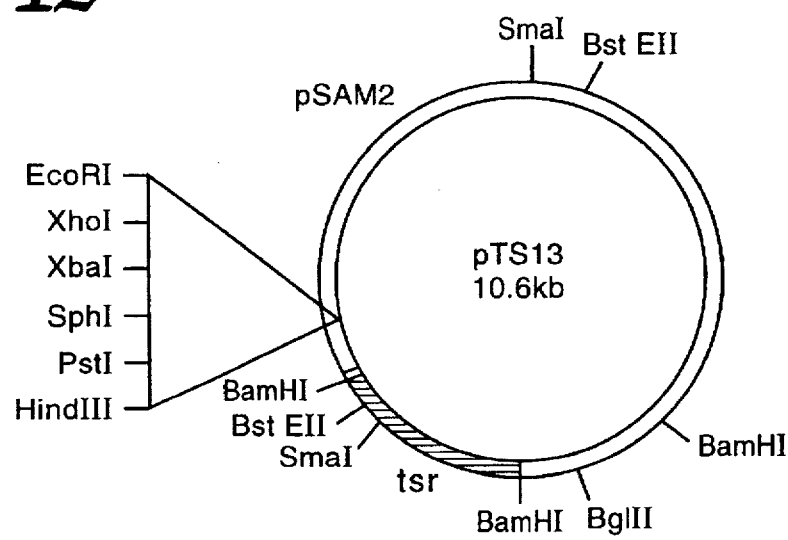
FIG. 12 shows the restriction chart of plasmid pTS13.

It is mixed with the fragment BglII of pTS11 and ligatured. The resulting plasmid which carries the oligonucleotide inserted at BglII No 14 is called pTS12 (FIG. 11) and that which bears the oligonucleotide inserted at the site BglII No 28 is called pTS13 (FIG. 12).

In the same manner it would be possible to insert a polylinker in the sites BamHI bounding the fragment BamHI of 1.79 kb bearing the resistance gene of Thiostreptide.

The properties of the vectors obtained are as follows:

These vectors due to the deletion on each side of the EcoRI No 33 site of pSAM2 are maintained at a very high level of copies since they are introduced into Streptomyces and especially *Streptomyces lividans* TK64. The number of copies is greater than 100 per genome.

They confer resistance on Thiostrepton and bear the cloning sites HindIII, PstI, SphI, XbaI, XhoI and EcoRI.

The vector pTS13 is incapable of being integrated into the chromosome and is only autoreplicating.

The vector pTS12 should no longer be capable of being transferred and would no longer be conjugating.

Any vector derived from pSAM2 containing this deletion passes from about 10 copies to more than 100 copies.

EXAMPLE 4

Expression of an alpha-amylase gene of *Streptomyces limosus* by using an integrating derivative of the plasmid pSAM2 Construction Method The Omega interposon confering resistance to the antibiotic spectinomycin (Prentki and Kirsh, 1984, Gene 29, p. 303–312) was inserted at the EcoRI site of the plasmid pOS210 A of FIG. 4. A fragment bearing the structural gene of the alpha-amylase of *S. limosus* as well as the promota sequences (Long et at., 1987, Journal of bacteriology 169, p. 5745–5754) (this gene has been patented by the Cetus Company) were inserted at the BamHI site of the resulting plasmid. This recombinant plasmid was introduced by transformation into *S. lividans*. The transformants selected for resistance to the antibiotic spectinomycin are very stable and produce alpha-amylase without selection pressure to maintain the recombinant plasmid integrated.

BIBLIOGRAPHY

Batlz R. H., Seno E. T., Stonesifer J. and Wild G. M. (1983) Biosynthesis of the macrolide antibiotic tylosin a preferred pathway from tylactone to tylosin. J. of Antibiotics 36 n° 2 131–141.

Cox K. L., Baltz R. H. (1984) Restriction of Bacteriophage plaque formation in Streptomyces ssp. J. Bact. 159.

Gray G., Seltzer G., Buell G., Shaw P., Escanez S., Hofer S., Voegeli P. and Thompson C. J. (1984) Synthesis of bovine growth by *Streptomyces lividans*. Gene 1124, 21–30.

Kuhstoss S., and Nagaraja Rao R. (1983) Expression in *Streptomyces ambofaciens* of an *Escherichia coli* K-12 gene which confers resistance to hygromycin B. Gene 26, 295–299.

Matsushima P., Baltz R. H. (1995) Efficient plasmid transformation of *Streptomyces ambofaciens* and *Streptomyces fradiae* protoplasts. J. Bact. 163, 180–185.

Omura S. (1984) Macrolide Antibiotics: Chemistry, Biology and Practice. Academic Press.

Covarrubias L., Bolivar F. (1982) Construction and characterization of new cloning vehicles. VI. Plasmid pBR329, a new derivative of pBR328 lacking the 482 base-pair inverted duplication. Gene 17: 79–89.

We claim:

1. A vector for cloning and expressing a DNA molecule encoding a particular protein in a strain of Actinomycetes, consisting of:

an att attachment DNA molecule selected from the group consisting of
TTCTCTGTCGGGGTGGCGGGATTTGAAC-CCACGACCTCTTCGTCCCGAA and a DNA molecule which hybridize to it in *S. antibioticus* (DSM 40868), *S. bikiniensis* (ATCC 11062), *S. paryulus* (ATCC 12434), *S. glaucescens* (ETH 22794), *S. actuosus* (ATCC 25421), *S. coelicolor* (A3(2)), *S. ambofaciens*, *S. lividans* TK64 (66), and *S. griseofuscus* (DSM 40191);

a DNA molecule coding for an int protein functional in said strain consisting of the DNA depicted in FIG. 3; and a DNA molecule encoding said particular protein operably linked to a promoter wherein said DNA molecule encoding said particular protein is inserted into said DNA molecule coding for said int protein wherein said vector is a plasmid and said att DNA molecule, said DNA molecule coding for said int protein and said DNA molecule are positioned in said vector such that the DNA is expressed in the strain.

2. A DNA molecule coding for an int protein functional in a strain of Actinomycetes consisting of the DNA depicted in FIG. 3.

3. The plasmid according to claim 1 wherein the DNA molecule according for said protein is a DNA molecule coding for resistance to thiostrepton.

Figure 1:
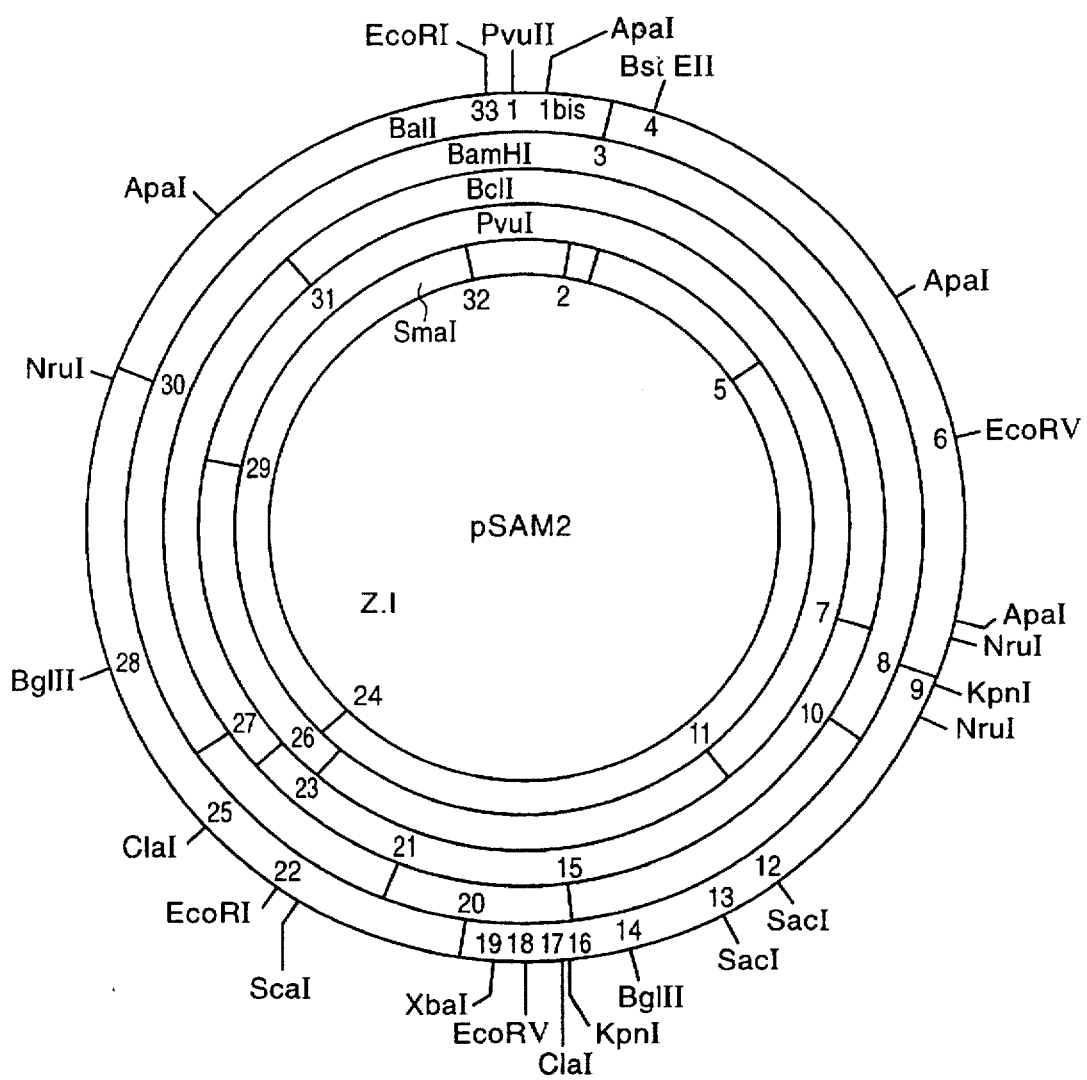
FIG. 1 shows the restriction chart of the plasmid pSAM2: the restriction sites are numbered from 1 to 33, the first is PvuII (no 1), the last is EcoRI (no33)

4. A vector for cloning and expressing a DNA molecule encoding a particular protein in a strain of Actinomycetes, consisting of:

an att attachment DNA molecule selected from the group consisting of
TTCTCTGTCGGGGTGGCGGGATTTGAAC-CCACGACCTCTTCGTCCCGAA and a DNA molecule which hybridize to it in *S. antibioticus* (DSM 40868), *S. bikiniensis* (ATCC 11062), *S. paryulus* (ATCC 12434), *S. glaucescens* (ETH 22794), *S. actuosus* (ATCC 25421), *S. coelicolor* (A3 (2)), *S. ambofaciens*, *S. lividans* TK64 (66), and *S. griseofuscus* (DSM 40191);

a DNA molecule coding for an int protein functional in said strain consisting of the DNA depicted in FIG. 3; and a DNA molecule encoding said particular protein operably linked to a promoter;

wherein said att DNA molecule, said int encoding DNA molecule and said DNA molecule are positioned in said vector such that the DNA is expressed in the strain and said att corresponding to
TTCTCTGTCGGGGTGGCGGGATTTGAAC-CCACGACCTCTTCGTCCCGAA and int DNA molecules are obtained from a pSAM2 fragment which has been deleted from about 600 bp on each side of the EcoRI No 33 site shown in FIG. 1.

5. A vector for cloning and expressing a DNA molecule encoding a particular protein in a strain of Actinomycetes, consisting of:

an att attachment DNA molecule selected from the group consisting of
TTCTCTGTCGGGGTGGCGGGATTTGAAC-CCACGACCTCTTCGTCCCGAA and a DNA molecule which hybridize to it in *S. antibioticus* (DSM 40868), *S. bikiniensis* (ATCC 11062), *S. paryulus* (ATCC 12434), *S. glaucescens* (ETH 22794), *S. actuosus* (ATCC 25421), *S. coelicolor* (A3 (2)), *S. ambofaciens*, *S. lividans* TK64 (66), and *S. griseofuscus* (DSM 40191);

a DNA molecule coding for an int protein functional in said strain consisting of the DNA depicted in FIG. 3; and a DNA molecule encoding said particular protein operably linked to a promoter;

wherein said att DNA molecule, said int encoding DNA molecule and said DNA molecule are positioned in said vector such that the DNA is expressed in the strain and wherein the DNA molecule encoding the particular protein is present in said vector outside said att attachment DNA molecule and outside said DNA molecule coding for an int protein and is inserted in DNA molecules coding for transfer functions and wherein said introduction is effected under conditions such that said DNA molecule is expressed and said encoded protein is thereby produced.

* * * * *